(12) United States Patent
DuBois et al.

(10) Patent No.: US 6,990,981 B2
(45) Date of Patent: Jan. 31, 2006

(54) PROTECTIVE EYEWEAR FOR HEALTHCARE PROVIDERS

(75) Inventors: Gene DuBois, Wellesley, MA (US); Alan Kenneth Stratton, Merrimack, NH (US)

(73) Assignee: Embrace Healthcare, Nashua, NH (US)

( * ) Notice: Subject to any disclaimer, the term of this patent is extended or adjusted under 35 U.S.C. 154(b) by 0 days.

(21) Appl. No.: 10/662,148

(22) Filed: Sep. 12, 2003

(65) Prior Publication Data
US 2005/0055751 A1    Mar. 17, 2005

(51) Int. Cl.
*A61F 9/00*    (2006.01)

(52) U.S. Cl. .................. 128/858; 2/9; 2/426; 2/429

(58) Field of Classification Search ............... 2/9, 2/15, 426, 429; 128/858, 857
See application file for complete search history.

(56) References Cited

U.S. PATENT DOCUMENTS

| | | |
|---|---|---|
| 1,706,667 A | 3/1929 | Haustein |
| 2,342,982 A | 2/1944 | Stern et al. .................... 2/9 |
| 2,527,027 A | 10/1950 | Mull ............................ 2/14 |
| D170,033 S | 7/1953 | Spencer ...................... 57/1 |
| 2,774,970 A | 12/1956 | Du Bois ....................... 2/9 |
| 2,866,202 A | 12/1958 | Landis ......................... 2/12 |
| 3,233,249 A | 2/1966 | Baratelli et al. .............. 2/14 |
| 4,470,673 A | 9/1984 | Gilson et al. ................ 351/44 |
| 4,542,964 A | 9/1985 | Gilson et al. ................ 351/44 |
| 4,670,915 A | 6/1987 | Evans ......................... 2/450 |
| 4,815,838 A | 3/1989 | Liautaud .................. 351/158 |
| 4,843,655 A | 7/1989 | Hegendörfer ............... 2/449 |
| 4,852,189 A | 8/1989 | Duggan ...................... 2/452 |
| 4,884,296 A | 12/1989 | Nix, Jr. ........................ 2/11 |
| 4,898,460 A | 2/1990 | Magninat et al. .......... 351/114 |
| 4,917,479 A | 4/1990 | Bidgood .................... 351/123 |
| 4,945,574 A | 8/1990 | Dagher .......................... 2/9 |
| 4,972,521 A | 11/1990 | Lison ............................. 2/9 |
| 5,012,527 A | 5/1991 | Michel ........................... 2/9 |
| 5,113,529 A | 5/1992 | Carr ............................ 2/13 |
| 5,297,298 A | 3/1994 | Salatka et al. ............... 2/447 |
| 5,387,949 A | 2/1995 | Tackles ..................... 351/121 |
| 5,704,349 A | 1/1998 | Hubbard et al. ....... 128/206.19 |
| 5,781,271 A * | 7/1998 | Wheeler .................... 351/121 |
| 5,862,530 A | 1/1999 | Shillington ................. 2/439 |
| 6,345,892 B2 | 2/2002 | Nakamura ................. 351/103 |
| 6,375,324 B2 | 4/2002 | Schleger et al. .......... 351/121 |
| 6,481,845 B1 * | 11/2002 | Gazzara ....................... 351/62 |

OTHER PUBLICATIONS

Embrace, Cool Shieldz Protective Glasses product information, 1 pg., 2002.
DeRoyal, SPEYES Splash Protection for Eyes product information, 1 pg., 2002.
Embrace, Cool Shieldz, Solid Side Shields, Protective Face Masks product information, 1 pg., 2002.
Embrace, Disposable Eye Shield product information, 1 pg., 2001.

* cited by examiner

*Primary Examiner*—Henry Bennett
*Assistant Examiner*—Camtu Nguyen
(74) *Attorney, Agent, or Firm*—Mark S. Leonardo; George S. Haight, IV; Brown Rudnick Berlack Israels

(57) ABSTRACT

Eyewear with a disposable shield that is OSHA compliant with no holes or perforations in the side shields. This protective eyewear consists of a flexible, anti-fog, anti-glare coated disposable material to maximize protection of a wearer's eyes and face from splashes, sprays, spatter or droplets of blood or other potentially infectious materials while giving the wearer a maximum range of vision.

11 Claims, 3 Drawing Sheets

PROTECTIVE EYEWEAR FOR HEALTHCARE PROVIDERS

FIELD OF THE INVENTION

The present invention relates to protective eyewear, more specifically disposable protective eyewear to protect a wearer from splashes, sprays, spatter or droplets of blood or other potentially infectious materials.

BACKGROUND OF THE INVENTION

Protective eyewear in infectious environments, such as hospitals and operating rooms, is imperative to protect employees from hazardous exposure when working. Occupational Safety and Health Administration (OSHA) regulation 1910.1030 (d)(x) requires employees to wear protective masks and eyewear whenever splashes, spray, spatter, or droplets of blood or other potentially infectious materials may be generated and eye, nose, or mouth contamination can be reasonably anticipated. The regulations require the eyewear be either full length face shields or glasses or goggles with solid side shields.

Many healthcare supply manufacturers have made and sold goggles and masks, however these devices are prone to fogging and are costly. Known products are not comfortable nor do they possess the stylish appearances. They are also difficult to clean, further enhancing the possibility of exposure to infectious materials. In light of these risks, disposable protective eyewear has become more prevalent in environments containing infectious materials. These disposable glasses are typically a single unit containing a protective shield and a frame. The lenses must be disposed of in order ensure a sanitary environment, although the frame may be sterilized and reused. The ability to reuse the frame makes it more cost-effective.

Other low cost disposable eyewear products consist of a removable shield that slides on and off the frame through holes in the sides of the shield. While this does provide a cost effective solution, the holes perforated in the shield allow for passage of infectious materials through the eyewear and onto the face or into the eye. This raises issues with respect to OSHA compliance. Another hazard presented by known disposable eyewear is an opening directly above the eyes between the forehead and the frame of the eyewear. This exposes the wearer to splatters and sprays that may come from above the sightline of the wearer.

SUMMARY OF THE INVENTION

The present invention provides affordable, anti-fog coating on both sides of the disposable eye shield, anti-glare, protective eyewear that maximizes protection of the eyes and face from infectious materials, while giving the wearer a maximum range of vision. In addition to maximizing protection, the present invention presents eyewear with a disposable shield that is OSHA compliant with no holes or perforations in the side shields.

In one embodiment of the present invention, a molded plastic frame is made in a substantially U-shaped design. Two bends at the closed end of the frame have guards extending from the frame inward that will rest against the forehead of the wearer. The outside of the frame contains projections intermittently spaced which engage with mating structures on an eye shield, attaching the eye shield to the frame to protect the eyes and face. The eye shield is a thin plastic sheet, cut to include a notch for the wearer's nose. It is coated on both sides with an anti-fogging material. A color band may be built into the top of the eye shield for easy gripping and identification. The top of the shield contains the mating structures in the form of small holes intermittently spaced that snap over the projections on the outside of the frame to attach the shield to the frame.

Advantages of the present invention include provision of eye protection that is compliant with OSHA standards. There are no exposure holes in the eye shield through which infectious materials may pass. The eye shield is held in place by use of a tapered knob that attaches it to the frame without damaging the lens or creating any opening. The protective eyewear according to the present invention eliminates exposure points around the eyes and temples of the wearer.

Another advantageous feature is the present invention provides a cost effective solution to protective eyewear by utilizing disposable eye shields while being able to re-use the frames.

An additional advantage of the present invention is the creation of space between the wearer's eyes and the eye shield sufficient to permit the wearing of typical prescription glasses under the protective eyewear.

Another advantageous feature of the present invention is the ease of interchangeability of the eye shield. The eye shield snaps along the outside of the frame making it easier and faster to remove and replace when needed without creating fingerprints or smudges on the eye shield. The positioning of the tapered knob and the angle of the lens due to the use of the shelf on the frame results in a lens angle that substantially eliminates glare. The frame is wide on the outside near the temples which naturally conforms to the human head.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

Figure 1:
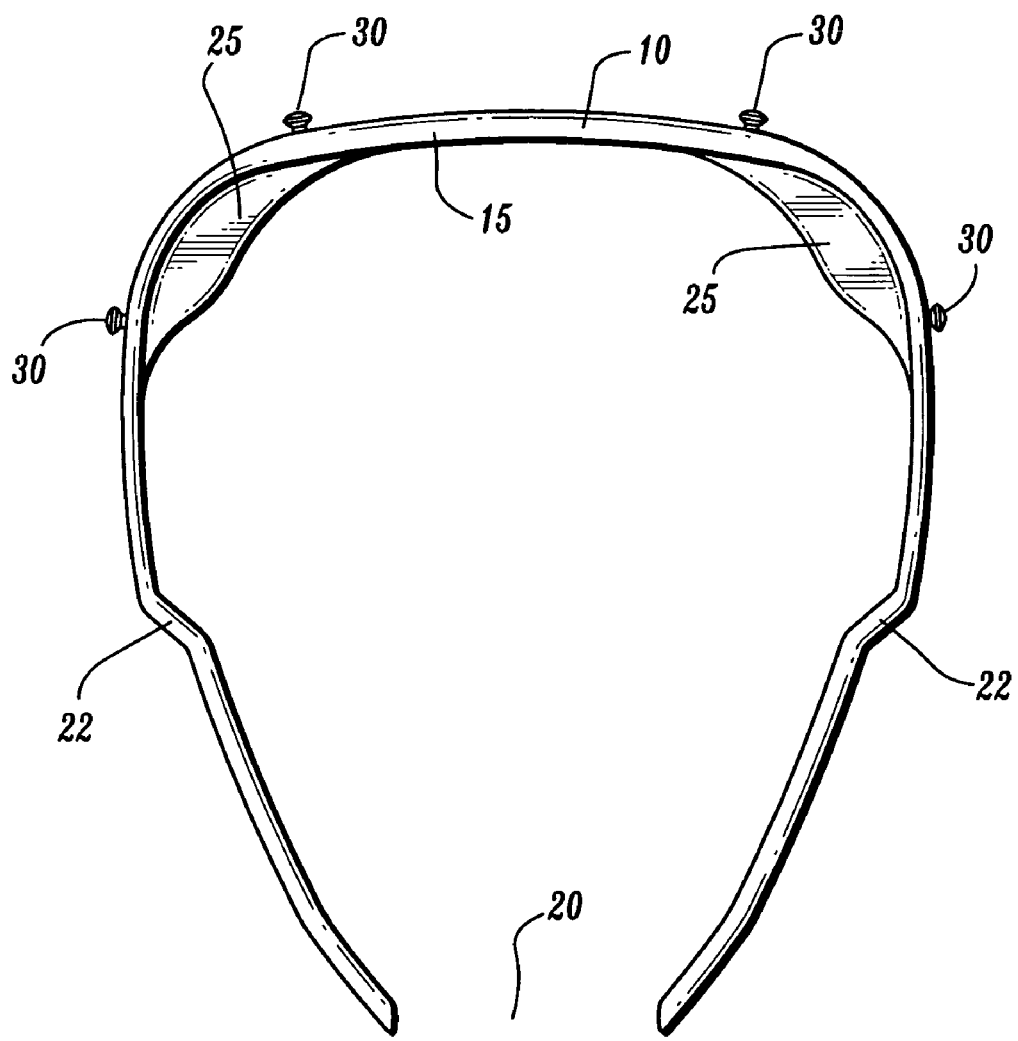
FIG. 1 is a top-down view of the frame in accordance with one embodiment of the present invention.

An embodiment of a frame for protective eyewear according to the invention is depicted in FIG. 1. The flexible frame 10 is made from a molded plastic and is substantially U-shaped with a closed end 15 and an open end 20. The flexible frame 10 is shaped in a wrap-around form where the natural form of the flexible frame holds the open end 20 smaller than the width of the average wearers head. This results in a constant tension inward on the wearer's head to hold the frame 10 in place and prevent it from slipping off the wearer's head. The frame 10 has angle points 22 whereat the frame 10 extends or angles forming a gripping area at the angle points 22 to allow the user to grip the eyewear to put it on or remove it. The angle points also the align the frame 10 with the contours of the wearer's head.

The inside corners of the closed end 15 of the frame 10 are formed with guards 25 extending inwardly from the frame 10. The guards 25 abut the wearer's head just above the eye socket when the protective eyewear is worn, and protect the wearer from infectious materials that may spray, splatter, or drip from above the wearer's sightline. The frame 10 has a plurality of projections 30 disposed around the exterior of the frame 10 along the closed end 15.

Figure 2:
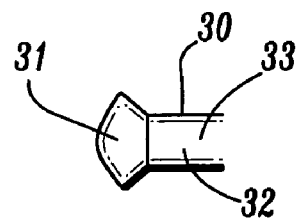
FIG. 2 is a detached and enlarged view of a projection in accordance with one embodiment of the present invention.

Now referring to FIG. 2, an illustrative projection 30 in this embodiment has a generally oval head 31. A cylindrical body 32 supports the oval head 31 and is smaller in diameter than the oval head 31. The oval head 31 and the cylindrical body 32 forming the projection 30 are molded as an integral part of the frame 10 and connect at a base 33 of the body 32.

Figure 3:
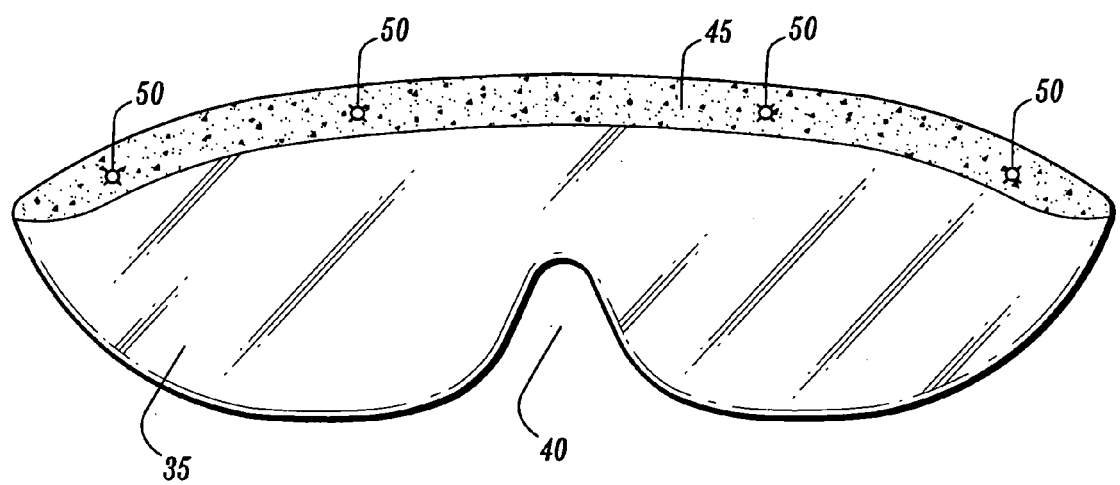
FIG. 3 is a frontal view of the eye shield before attachment to the frame in accordance with one embodiment of the present invention.

In an embodiment, as depicted in FIG. 3, an eye shield 35 portion of the protective eyewear is made from a lightweight, thin, clear polyester, plastic material. The eye shield 35 is a generally oval shape with a central notch 40, where the eye shield 35 will rest on the wearer's nose. The eye shield 35 is coated, on both surfaces, with anti-fogging material such as known in the art. The eye shield 35 may also be treated to eliminate glare and static electricity as known in the art. A colored band 45 is located on the top of the eye shield 35. The colored band 45 may be silk-screened on to the eye shield 35. The colored band 45 provides an easily grippable portion of the eye shield 35 for the user to touch without creating fingerprints, smudges, or other obstructions on the remainder of the eye shield 35. The eye shield 35 may be a variety of transparent shades depending on the environment in which the protective eyewear is used. Certain colors may enhance detailed viewing. The shield may be tinted red, orange, yellow, green, blue, indigo, violet, gray or any permutation thereof. The eye shield 35 also contains mating structures in the form of holes 50, for attaching the eye shield 35 to the corresponding mating structures (i.e. the projections on the frame 10).

Figure 4:
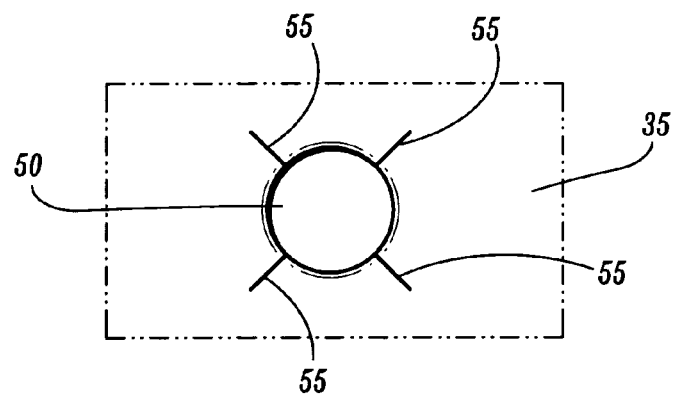
FIG. 4 is a frontal view of a hole with radial slits in the eye shield in accordance with one embodiment of the present invention.

Referring now to FIG. 4, the holes 50 are located at the top of the eye shield 35, in the colored band 45 in this embodiment. The holes 50 align with the projections 30 along the frame 10. The diameter of the holes 50 is substantially equal to the diameter of the body 32 of the projection 30. Radial slits 55 around the holes 50 allow the holes 50 to expand and snap securely over the projections 30. When the holes 50 are in position over the projections, the radial slits 55 no longer expand the holes 50, eliminating any exposure points through the eye shield 35 when it is attached to the frame 10.

Figure 5:
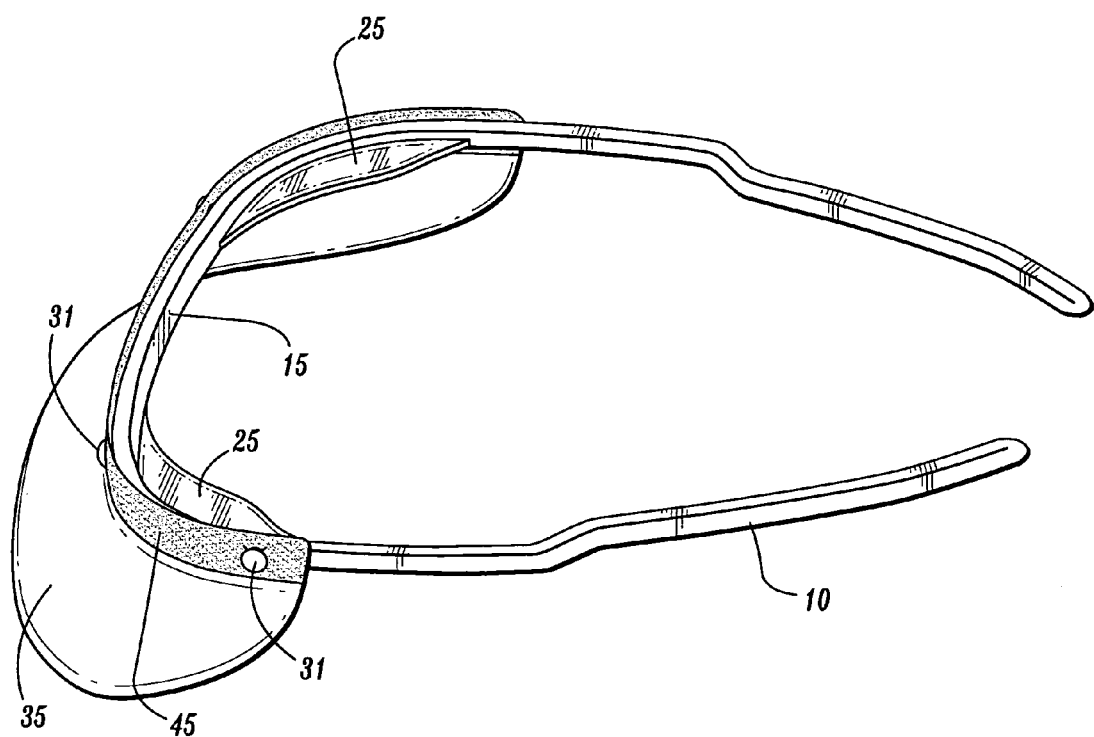
FIG. 5 is a perspective view of an assembled eye shield in accordance with one embodiment of the present invention.

FIG. 5. illustrates the resulting combination of attaching the eye shield 35 to the frame 10 forming a cost effective, reliable, safe and compliant form of protective eyewear. When the eye shield is attached to the frame the holes 50 no longer expand and the oval heads 31 of the projections 30 retain the eye shield 35 in assembly with the frame 10. When assembled with the frame 10, the eye shield 35 wraps around the closed end 15 of the frame 10 to provide solid protection to the side of the eye area as required by OSHA standards. When assembled, the combination of the downward angle of the eye shield 35 relative to the frame 10, and the guards 25 that abut the wearer's head, create spacing sufficient to permit regular prescription glasses to be worn under the protective eyewear according to the invention. The downward angle of the eye shield 35 also helps to eliminate the glare from surrounding lights. When the wearer needs to replace the eye shield 35, the wearer simply grips the eye shield 35 at the color band 45 and pulls the eye shield over the oval heads 31 and off the projections 30. The wearer then obtains a replacement eye shield 35 and, while gripping the eye shield 35 at the color band 45, re-engages the holes 50 with the projections by snapping the holes 50 over the oval heads 31 of the projections 30. This alleviates the need for a completely new eye protection unit while remaining safe and effective against infectious materials.

Although the embodiments described herein describe a frame that is substantially U-shaped, it should be appreciated by those skilled in the art that various shapes of frames can be used (e.g., square, angular, circular). Additionally while two bends in the closed end of the frame are discussed, it should be appreciated by those skilled in the art that different numbers of bends can be made in the frame without departing from the spirit of the invention.

Although the embodiments herein describe mating structures comprising expanding holes and projections, it should be appreciated by one skilled in the art that other mating structures can be used (e.g., projections on the eye shield engaging with corresponding holes in the frame, VELCRO strips, adhesive strips, channel or slot fitting or the like).

Additionally, while the illustrative embodiments herein describe projections having a head and a body having a smaller diameter than the head, one skilled in the art should appreciate that other retaining structures may be used on the projections, such as tangs extending from the projection or a notch on the projection for receiving the mating structure of the transparent shield.

Although the invention is described hereinbefore with respect to illustrative embodiments thereof, persons having ordinary skill in the art should appreciate that the foregoing and various other changes, omissions and additions in the form and detail thereof may be made without departing from the spirit and scope of the invention.

What is claimed is:

1. An apparatus for protecting a wearer's eyes and face from contact with infectious materials comprising:

a flexible frame having an outside surface;

at least one guard extending inwardly from the flexible frame, the at least one guard configured to abut the wearer's forehead when the apparatus is positioned on the wearer's head;

a plurality of projections spaced along the outside surface of the flexible frame, the projections having a head and a body; and a transparent shield having a first portion, the first portion of the transparent shield defining a plurality of expandable openings, the expandable openings having a non-expanded size smaller than that of the head of the projections, the expendable openings providing a snap-fit over the projections, leaving no opening or space once the projection has been fit with the expandable opening.

2. The apparatus of claim 1, wherein each projection has a substantially circular head and a substantially circular body, the head having a diameter, the body having a diameter less than the diameter of the head; and the openings have a diameter substantially equal to the diameter of the body of the projections, the openings having radial slits extending outwardly, the openings expanding to snap over the head of the projections.

3. The apparatus of claim 1, wherein the plurality of projections and the at least one guard comprise a single unit of molded plastic.

4. The apparatus of claim 1, wherein the flexible frame comprises steps angled inwardly for a distance forming a gripping area.

5. The apparatus of claim 1, wherein the at least one guard comprises a first guard extending inwardly from the flexible frame along a first corner, a second guard extending inwardly from the flexible frame along a second corner.

6. The apparatus of claim 1, wherein the transparent shield comprises a second portion defining a notch for resting on a wearer's nose.

7. The apparatus of claim 1, wherein the transparent shield comprises a polyester material.

8. The apparatus of claim 1, wherein the transparent shield comprises of a plastic material.

9. The apparatus of claim 1, further comprises: an indicator band disposed along the top portion of the transparent shield for providing a gripping surface.

10. The apparatus of claim 1, wherein the transparent shield comprises a front surface and a back surface, the front surface and the back surface coated with an anti-fogging material.

11. The apparatus of claim 1, wherein the transparent shield is tinted a color selected from the group consisting of red, orange, yellow, green, indigo, violet, and grey.

* * * * *